United States Patent [19]

Porter et al.

[11] Patent Number: 4,543,370

[45] Date of Patent: Sep. 24, 1985

[54] DRY EDIBLE FILM COATING COMPOSITION, METHOD AND COATING FORM

[75] Inventors: Stuart C. Porter, Hatfield; Edward J. Woznicki, Douglassville, both of Pa.

[73] Assignee: Colorcon, Inc., West Point, Pa.

[21] Appl. No.: 202,831

[22] Filed: Nov. 6, 1980

Related U.S. Application Data

[63] Continuation-in-part of Ser. No. 98,531, Nov. 29, 1979, abandoned.

[51] Int. Cl.$^4$ ................................................ C08J 3/12
[52] U.S. Cl. ...................................... 523/100; 523/105; 424/33; 424/34; 106/193 J; 106/193 P; 106/149
[58] Field of Search ............ 106/154 Z, 193 D, 193 J, 106/193 P; 260/31.8 R, 29.6 H, 33.4 R, 32.8 R, 33.8 UA; 424/33–36; 523/100, 105; 8/524

[56] References Cited

U.S. PATENT DOCUMENTS

| | | | |
|---|---|---|---|
| 3,149,040 | 9/1964 | Jeffries | 424/35 |
| 3,297,535 | 1/1967 | Butler et al. | 424/34 |
| 3,576,663 | 4/1971 | Signorino et al. | 424/34 |
| 3,835,221 | 9/1974 | Fulborth et al. | 424/33 |
| 3,981,984 | 9/1976 | Signorino | 260/33.4 R |
| 4,009,131 | 2/1977 | Farone | 260/31.8 R |
| 4,015,999 | 4/1977 | Robertson | 106/193 D |
| 4,112,215 | 9/1978 | Boessler | 523/100 |
| 4,295,851 | 10/1981 | Neumann et al. | 8/524 |
| 4,330,338 | 5/1982 | Banker | 424/33 |

*Primary Examiner*—Paul R. Michl
*Attorney, Agent, or Firm*—John F. A. Earley; John F. A. Earley, III

[57] ABSTRACT

A dry powder edible film coating composition for use in pharmaceuticals, confectionery and food, comprising a dry mixture including powdered particles of a film forming non-toxic polymer, powdered edible pigment particles, and an edible polymer plasticizer, said dry mixture being solvent free. A method of making a dry powder edible film coating composition of powdered pigment particles for use in pharmaceuticals, confectionery and food, comprising the steps of mixing a powder of a film forming polymer and powdered pigment particles in a blender to form a polymer-pigment mix, and adding the plasticizer to the blender containing the polymer-pigment mix and mixing until the combined mix is blended to form the dry powder edible film coating composition.

63 Claims, No Drawings

DRY EDIBLE FILM COATING COMPOSITION, METHOD AND COATING FORM

This is a continuation-in-part of our U.S. patent application Ser. No. 98,531, filed on Nov. 29, 1979, now abandoned.

TECHNICAL FIELD

This invention is in the field of coating of pharmaceutical tablets and the like, and provides a dry edible film coating composition for use in pharmaceuticals, confectionery, and food.

CROSS-REFERENCE TO RELATED PATENTS

This patent application is concerned with edible coating systems and is related to U.S. Pat. No. 3,981,984 which issued Sept. 21, 1976 to Charles A. Signorino, owned by Colorcon, Inc., West Point, Pa. 19486, the assignee of this patent application, and is incorporated herein by reference.

BACKGROUND OF THE INVENTION

Signorino U.S. Pat. No. 3,981,984 provides an edible concentrated pigment suspension that is shipped, for example, to a pharmaceutical manufacturer who mixes it with a polymer solution to form a coating suspension which may be used for coating tablets and the like. The pigment suspension, polymer solution, and coating suspension are in a non-aqueous solvent.

It has long been desired to provide a dry edible film coating composition which can be constituted with solvent by the customer, that eliminates the problem of shipping of pigment dispersions containing aqueous or non-aqueous solvents and thereby eliminates the problems caused by solvents, and also makes shipping less expensive by eliminating the weight of the solvents.

It is known in the prior art to mix a dry polymer powder with pigment particles, and to grind the mixture to obtain a dry polymer-pigment mixture which is then ground into a fine powder mixture. However, when this fine polymer-pigment mixture is stirred into water and dispersed, the polymer makes lumps and fish eyes because it agglomerates, and the result is not really a uniform dispersion. Accordingly, when this polymer-pigment dispersion is used as a coating dispersion and is coated onto tablets and the like, unless the dispersion is left to solvate for a considerable period of time like overnight, the coating is lumpy and not uniform and is therefore undesirable.

SUMMARY OF THE INVENTION

A dry edible film coating composition for use in pharmaceuticals, confectionery and food, comprising a mixture including polymer particles, pigment particles, and a polymer plasticizer. Advantageously, a surfactant may be added especially when the plasticizer may be a solid. The composition may also include a flow aid.

A method of making a dry edible film coating composition for use in pharmaceuticals, confectionery and food, comprises the steps of mixing a polymer powder and pigment particles in a blender, adding a plasticizer to the blender containing the polymer-pigment mix, and mixing until the combined mix is thoroughly blended. A surfactant may be mixed with the plasticizer, especially when the plasticizer is a solid. A flow aid may be mixed into the polymer-pigment mix, such as Cabosil (finely divided colloidal silica by Cabot Corp., Boston Mass.), or Aerosil (finely divided colloidal silica by Degussa, Frankfurt, W. Germany).

The polymer may be methylcellulose, hydroxypropyl methylcellulose, hydroxypropyl cellulose, cellulose acetate phthalate, ethylcellulose, polyvinylpyrrolidone, sodium ethylcellulose sulphate, zein, polyvinylacetatephthalate, methacrylic acid-methacrylic acid ester co-polymer, or other film forming polymer used for coating tablets and the like.

Any of the pigments heretofore used in making coating dispersions for coating tablets and the like may be used in the dry coating mixture of this invention. Examples are FD&C and D&C lakes, titanium dioxide, magnesium carbonate, talc, pyrogenic silica, iron oxides, channel black, and insoluble dyes. Also natural pigments such as riboflavin, carmine 40, curcumin, and annatto. Other examples are listed in Jeffries U.S. Pat. No. 3,149,040 and Butler et al. U.S. Pat. No. 3,297,535, as well as in Colorcon U.S. Pat. No. 3,981,984. All these patents and patent applications are incorporated herein by reference.

Exemplary of the polymer plasticizer for use in the dry coating mixture of the invention are polyethylene glycol, for example, polyethylene glycol having a molecular weight of 200 to 8000 (Carbowax by Union Carbide), glycerin, propylene glycol, Triacetin (Pfizer's glycerin triacetate), acetylated monoglyceride, and Citroflex 2 (triethylcitrate), Citroflex 4 (tributylcitrate citrate), Citroflex A2 (acetyltrithylcitrate), Citroflex A4 (acetyltributylcitrate), diethyl phthalate, and mineral oil. Citroflex 2, 4, A2 and A4 are made by Pfizer and are plasticizers adapted for use with organic solvents.

The polymer plasticizer, to soften the polymer and make it less brittle, may be a liquid or a solid plasticizer, and a preferred plasticizer is a liquid such as polyethylene glycol 400.

The surfactant may be, for example, a solid powder surfactant such as Aerosol OT (dioctyl sodium sulfosuccinate by Cyanimid) which is preferably used with the liquid polyethylene glycol 400, or Tween 80 (polysorbate 80 by ICI Americas, Wilmington, Del.) which is a liquid and is preferably used with a solid plasticizer such as the polyethylene glycol 3350 and 8000.

DETAILED DESCRIPTION

We now turn to the examples of the invention, all ingredients being in parts by weight:

EXAMPLE 1

1500 grams of a polymer, powdered hydroxypropyl methylcellulose, are mixed with 750 grams of a powdered pigment, titanium dioxide in a V blender, a P-K blender with an intensifier bar. Then 150 grams of a plasticizer, polyethylene glycol 400, are thoroughly mixed with 5 grams of a surfactant, dioctyl sodium sulfosuccinate. The polyethylene glycol 400 - dioctyl sodium sulfosuccinate mix is then added to the blender and thoroughly mixed with the mixture of hydroxypropyl methylcellulose and titanium dioxide to form a coating mixture. The resulting mixture is then passed through a grinder in order to reduce it to a fine powder which is adapted for shipping in dry form to a pharmaceutical manufacturer where it is dispersed in water to form a coating dispersion that is applied to tablets and dried to form a uniform film coating on the tablets.

The coating dispersion obtained when the coating mixture is mixed with the solvent is surprisingly fluid and uniform, and easy to apply to the tablets.

EXAMPLE 2

The method of Example 1 is followed except that the 750 grams of titanium dioxide powder are replaced by 375 grams of titanium dioxide and 375 grams of red iron oxide which are mixed into the hydroxypropyl methylcellulose in the blender before the plasticizer-surfactant mix of polyethylene glycol 400 and dioctyl sodium sulfosuccinate is added.

EXAMPLE 3

The method of Example 1 is followed except that the 750 grams of titanium dioxide powder are replaced by 499 grams of titanium dioxide, 75 grams of FD&C Yellow No. 6 aluminum lake, 25 grams of FD&C Red No. 3 aluminum lake, and 25 grams of FD&C Blue No. 2 aluminum lake.

EXAMPLE 4

The method of Example 1 is followed except that the 750 grams of titanium dioxide are replaced by 250 grams of titanium dioxide, 150 grams of FD&C Yellow No. 6 aluminum lake, 50 grams of FD&C Red No. 3 aluminum lake, and 50 grams of FD&C Blue No. 2 aluminum lake.

EXAMPLE 5

The method of Example 1 is followed except that the 750 grams of titanium dioxide are replaced by 83 grams of titanium dioxide, 199 grams of FD&C Yellow No. 6 aluminum lake, 67 grams of FD&C Red No. 3 aluminum lake, and 67 grams of FD&C Blue No. 2 aluminum lake.

EXAMPLE 6

The method of Example 1 is followed execpt that the 750 grams of titanium dioxide are replaced by 250 grams of titanium dioxide, 150 grams of FD&C Yellow No. 6 aluminum lake, 50 grams of FD&C Red No. 3 aluminum lake, and 50 grams of FD&C Blue No. 2 aluminum lake. Also, the 5 grams of dioctyl sodium sulfosuccinate are replaced by 5 grams of polysorbate 80 (Tween 80 by ICI Americas), another surfactant.

EXAMPLE 7

The method of Example 1 is followed except that the 750 grams of titanium dioxide are replaced by 250 grams of titanium dioxide, 150 grams of FD&C Yellow No. 6 aluminum lake, 50 grams of FD&C Red No. 3 aluminum lake, and 50 grams of FD&C Blue No. 2 aluminum lake. Also, 10 grams of fumed silica (Cabosil by Cabot Corp., Boston, Mass.) are added to the polymer-pigment mix to improve the flow in the grinder, and to improve the flow when the dry coating mixture is shipped in containers such as drums.

EXAMPLE 8

The method of Example 1 is followed except that the 750 grams of titanium dioxide are replaced by 250 grams of titanium dioxide, 150 grams of FD&C Yellow No. 6 aluminum lake, 50 grams of FD&C Red No. 3 aluminum lake, and 50 grams of FD&C Blue No. 2 aluminum lake.

EXAMPLE 9

The method of Example 1 is followed except that the 1500 grams of hydroxypropyl methylcellulose are replaced by 1500 grams of methyl cellulose (Methocel A15 by Dow Chemical Co.).

EXAMPLE 10

The method of Example 1 is followed except that 1500 grams of hydroxypropl methylcellulose are replaced by 1500 grams of hydroxypropyl cellulose (Klucel, by Hercules, Inc., Wilmington, Del.).

EXAMPLE 11

The method of Example 1 is followed except the 1500 grams of hydroxypropyl methylcellulose are replaced by 1500 grams of sodium ethyl cellulose sulphate.

EXAMPLE 12

The method of Example 1 is followed except the 150 grams of polyethylene glycol 400 liquid plasticizer are replaced by 150 grams of glycerin.

EXAMPLE 13

The method of Example 1 is followed except the 150 grams of the liquid plasticizer, polyethylene glycol 400 are replaced by 150 grams of propylene glycol.

EXAMPLE 14

The method of Example 1 if followed except the 150 grams of polyethylene glycol 400 are replaced by 150 grams of powdered polyethylene glycol 6000, and the 5 grams of Aerosol OT are replaced by 5 grams of Tween 80.

EXAMPLE 15

The method of Example 1 is followed except the 150 grams of polyethylene glycol 400 are replaced by 150 grams of powdered polyethylene glycol 8000, and the 5 grams of Aerosol OT are replaced by 5 grams of Tween 80.

EXAMPLE 16

1500 grams of a polymer, powdered hydroxypropyl methylcellulose are mixed with 750 grams of a powdered pigment, titanium dioxide in a V blender, a P-K blender with an intensifier bar. Then 150 grams of a plasticizer, polyethylene glycol 400, are added to the blender and thoroughly mixed with the mixture of hydroxypropyl methylcellulose and titanium dioxide to form a coating mixture. The resulting mixture is then passed through a grinder in order to reduce it to a fine powder which is adapted for shipping in dry form to a pharmaceutical manufacturer where it is dispersed in water to form a coating dispersion that is applied to tablets and dried to form a uniform film coating on the tablets.

EXAMPLE 17

The method of Example 16 is followed except that the 750 grams of titanium dioxide powder are replaced by 375 grams of titanium dioxide and 375 grams of red iron oxide which are mixed into the hydroxypropyl methylcellulose in the blender before the plasticizer polyethylene glycol 400 is added.

EXAMPLE 18

The method of Example 16 is followed except that the 750 grams of titanium dioxide powder are replaced by 499 grams of titanium dioxide, 75 grams of FD&C Yellow No. 6 aluminum lake, 25 grams of FD&C Red No. 3 aluminum lake, and 25 grams of FD&C Blue No. 2 aluminum lake.

EXAMPLE 19

The method of Example 16 is followed except that the 750 grams of titanium dioxide are replaced by 250 grams of titanium dioxide, 150 grams of FD&C Yellow No. 6 aluminum lake, 50 grams of FD&C Red No. 3 aluminum lake, and 50 grams of FD&C Blue No. 2 aluminum lake.

EXAMPLE 20

The method of Example 16 is followed except that the 750 grams of titanium dioxide are replaced by 83 grams of titanium dioxide, 199 grams of FD&C Yellow No. 6 aluminum lake, 67 grams of FD&C Red No. 3 aluminum lake, and 67 grams of FD&C Blue No. 2 aluminum lake.

EXAMPLE 21

The method of Example 16 is followed except that the 750 grams of titanium dioxide are replaced by 250 grams of titanium dioxide, 150 grams of FD&C Yellow No. 6 aluminum lake, 50 grams of FD&C Red No. 3 aluminum lake, and 50 grams of FD&C Blue No. 2 aluminum lake.

EXAMPLE 22

The method of Example 16 is followed except that the 750 grams of titanium dioxide are replaced by 250 grams of titanium dioxide, 150 grams of FD&C Yellow No. 6 aluminum lake, 50 grams of FD&C Red No. 3 aluminum lake, and 50 grams of FD&C Blue No. 2 aluminum lake. Also, 10 grams of fumed silica (Cabosil by Cabot Corp., Boston, Mass.) are added to the polymer-pigment mix to improve the flow in the grinder, and to improve the flow when the dry coating mixture is shipped in containers such as drums.

EXAMPLE 23

The method of Example 16 is followed except that the 750 grams of titanium dioxide are replaced by 250 grams of titanium dioxide, 150 grams of FD&C Yellow No. 6 aluminum lake, 50 grams of FD&C Red No. 3 aluminum lake, and 50 grams of FD&C Blue No. 2 aluminum lake.

EXAMPLE 24

The method of Example 16 is followed except that the 1500 grams of hydroxypropyl methylcellulose are replaced by 1500 grams of methyl cellulose (Methocel A15 by Dow Chemical Co.).

EXAMPLE 25

The method of Example 16 is followed except that 1500 grams of hydroxypropyl methylcellulose are replaced by 1500 grams of hydroxypropyl cellulose (Klucel, by Hercules, Inc., Wilmington, Del.).

EXAMPLE 26

The method of Example 16 is followed except the 1500 grams of hydroxypropyl methylcellulose are replaced by 1500 grams of sodium ethyl cellulose sulphate.

EXAMPLE 27

The method of Example 16 is followed except the 150 grams of polyethylene glycol 400 liquid plasticizer are replaced by 150 grams of glycerin.

EXAMPLE 28

The method of Example 16 is followed except the 150 grams of the liquid plasticizer, polyethylene glycol 400, are replaced by 150 grams of propylene glycol.

EXAMPLE 29

The method of Example 16 is followed except the 750 grams of titanium dioxide are replaced by 120 grams of titanium dioxide, 83 grams of FD&C Blue No. 1 aluminum lake, and 132 grams of riboflavin.

The optimum amount of plasticizer is about 10% of the polymer, as illustrated in Examples 1 and 16, for example. The preferred range is about 5% to 20% by weight of plasticizer to polymer, and a workable range is about 1% to 30% of plasticizer to polymer.

EXAMPLE 30

The method of Example 16 except the 150 grams of plasticizer are replaced by 75 grams.

EXAMPLE 31

The method of Example 16 except 15 grams of plasticizer are used instead of 150 grams.

EXAMPLE 32

The method of Example 16 except 300 grams of plasticizer are used instead of 150 grams.

EXAMPLE 33

The method of Example 16 except 450 grams of plasticizer replace the 150 grams of plasticizer.

The preferred polymer to pigment volume ratio is about 6.5 to 1 as is illustrated by Examples such as Examples 1 and 16. The ratio of polymer to pigment on a volume basis may vary between about 4 to 1 to 10 to 1.

EXAMPLE 34

The method of Example 16 except 923 grams of the polymer are used to give a volume ratio of polymer to pigment of 4 to 1.

EXAMPLE 35

The method of Example 16 is followed except that the 750 grams of titanium dioxide are replaced by 166 grams of titanium dioxide, 398 grams of Yellow No. 6 aluminum lake, 134 grams of FD&C Red No. 3 aluminum lake, and 134 grams of FD&C Blue No. 2 aluminum lake. The volume ratio of polymer to pigment is 4 to 1. Also, instead of 150 grams of the plasticizer, 300 grams are used. The plasticizer is 20% by weight of the polymer.

EXAMPLE 36

The method of Example 16 except 490 grams of red iron oxide are used instead of the 750 grams of titanium dioxide to give a volume ratio of polymer to pigment of 10 to 1, and 75 grams of the plasticizer are used instead of the 150 grams.

The preferred polymer to pigment ratio on a weight to weight basis is 3 to 1 as is illustrated by Example 4, but may vary between 2 to 1 as illustrated by Examples 1, 2, 16 and 17, and 5 to 1 as illustrated by Example 37.

EXAMPLE 37

The method of Example 16 except the 750 grams of titanium dioxide are replaced by 180 grams of FD&C Yellow No. 6 aluminum lake, 60 grams of FD&C Red No. 3 aluminum lake, and 60 grams of FD&C Blue No. 2 aluminum lake.

In regard to the surfactant, it may or may not be needed, depending on the plasticizer used. For example, when using plasticizers which are normally solids under processing conditions, the use of a surfactant can facilitate processing and subsequent constitution of the dry coating system with the solvent. Under these circumstances, from 0.2 to 2% of a non-toxic FDA approved surfactant was found to be advantageous.

As to particle size, the pigment particle size range may be between about 0.1 to 40 microns. The optimum mean particle size range for iron oxides is about 0.5 to 1 micron, for lakes and insoluble dyes is from about 1 to 5 microns, for titanium dioxide is about 0.5 to 2 microns, and for channel black is about 0.2 to 1 micron.

The methyl cellulose of Example 9 is Methocel A15 by Dow Chemical Co. Methocel E15 or E5 (also by Dow) may be used in place of Methocel A15.

The liquid plasticizers when used in making up the inventive dry coating mixture seem to have surfactant properties. The liquid plasticizers seem to act as a solvent for the surfactants, when used, and seem to disperse the surfactants throughout the system.

It is to be noted that the polymer to pigment ratio is a fixed ratio on a volume basis, not on a weight basis. The ratio of polymer to pigment on a volume basis is from about 4 to 1 to 10 to 1 with the preferred ratio being about 6.5 to 1. The volume ratio is used because of the different densities of the various lakes compared to the very dense titanium dioxide. The specific gravity of titanium dioxide to aluminum lakes is roughly about 4 to 2. If a lake of lesser density than titanium dioxide were substituted for an equal weight of titanium dioxide, you would get a greater volume of lake particles and you could get a situation where there would not be enough polymer to bind all the lake particles, which is undesirable. So for loading pigment particles into a polymer, a volume ratio is more satisfactory than a weight ratio.

We want the highest pigment loading possible. A preferred loading of 3 parts dry polymer to 1 part of pigment mixture of titanium dioxide and aluminum lake, by weight, gives a 50-50 ratio by weight of titanium dioxide to aluminum lake. This mixture is about 6.5 to 1 of polymer to pigment on a volume basis. We calculate the volume of that pigment mixture, and use that volume of pigment mixture no matter what pigments are used in the dry pigment mixture and the dry coating mixture. This provides about the same surface area of pigment to be bound by the polymer, no matter what pigments are dispersed in the polymer.

If you put too much pigment into the polymer, you do not have enough polymer to bind the pigment particles. If you put in too little pigment into the polymer, when you put the polymer-pigment mix into water you get a weak color which when applied to a tablet would produce a non-uniform color coating unless many layers of coating were applied.

Referring to the Examples, in Example 2, 375 grams of titanium dioxide were replaced by an equal volume of 375 grams of red iron oxide. In Example 3, 251 grams of titanium dioxide were replaced by an equal volume of 125 grams of aluminum lakes. In Examples 4, 6, 7 and 8, 500 grams of titanium dioxide were replaced by 250 grams of aluminum lakes. In Example 5, 667 grams of titanium dioxide were replaced by 333 grams of aluminum lakes.

ADVANTAGES

One advantage of the dry edible film coating system of the invention is that it breaks down and disperses out the polymer so that when you add the dry coating mixture to a solvent, the polymer does not agglomerate and form fish eyes or lumps. The pigments in this dry system are more efficiently dispersed throughout the polymer that even the non-aqueous OPASPRAY system described in Colorcon U.S. Pat. No. 3,981,984. The colors produced by the dry system are much darker, which shows that the dry system can be brought to the desired shade easily by using less pigment.

Also, the plasticizer seems to have surfactant properties which aid in the thorough dispersion of the dry coating mixture into the liquid coating dispersion.

The dry system of the invention has another advantage in that it eliminates warehousing problems caused by storing liquid pigment dispersions, such as susceptibility to changes because of heat, cold and bacteria, and also eliminates shelf-life problems caused by the solvent in liquid pigment dispersions.

The dry system when constituted in water has a viscosity lower than that of a conventional polymer coating system colored with an OPASPRAY pigment dispersion and having the same total solids and same polymer-pigment ratios so that for equivalent final dispersion viscosities a coating dispersion can be produced from the dry system which has a higher solids loading and consequently a lower solvent content.

The dry coating mixture of the invention is designed primarily for use in an aqueous system but it may also be used in a non-aqueous system with an appropriate polymer plasticizer, and with an organic solvent such as a mixture of methylene chloride and alcohol.

The superior fluidity and dispersion of the coating dispersion made from the dry coating mixture is new and surprising. Why this result is obtained is not presently clearly understood. This art is hightly unpredictable. For example, if we mix Cabosil into Klucel (hydroxypropyl cellulose by Hercules, Inc.), the mixture gums up the grinder. However, if we mix Cabosil into Methocel (hydroxypropyl methyl cellulose by Dow Chemical), the mix works just fine and does not gum up the grinder.

Another advantage of the dry system is that it reduces the amount of dust that usually is connected with the use of lakes because the plasticizer acts as a non-dusting coat on the pigment particles.

The method of this dry system provides a really superior dispersion of the ingredients of the dry coating mixture which is much better dispersed into a solvent to form a coating dispersion simply by adding the coating mixture to a solvent, such as water.

As to the commercial aspects of the invention, the dry coating mix eliminates selling a liquid solvent such as water, shipping water, and preserving water, which is required by the prior art wet systems. The water in this dry system is added to the dry coating mixture at its destination by the customer.

The coating mixture of this dry system may be used within an hour of its being made up; it does not require a waiting period such as overnight, as was required by the prior art aqueous and non-aqueous systems. Also, the dry system does not require high sheer mixers, nor non-dusting equipment. The coating dispersions made from the dry coating mixture may be sprayed within an hour of its being made up.

The final coating dispersion prepared from the dry system has a noticeably lower viscosity than a conventionally prepared system having the same ratios and levels of ingredients. There is about a 30% reduction of viscosity over the prior systems, so that the inventive dry coating system can be incorporated into the solvent at a higher solids level for spraying onto tablets, thus resulting in a lower quantity of water having to be sprayed and dried. This substantial lowering of viscosity of the coating dispersion made from the dry system is totally unexpected.

Although the polymer and pigment are completely mixed in the dry state and in the final applied coating, in the wet state the pigment is wetted to a lesser degree by the water than in a conventionally prepared system and thus is less viscous than would normally be expected.

In some areas, the shipping of alcohol-containing products by air is prohibited, so such products must be shipped by boat which takes much longer. Accordingly, the dry coating mixture of the present invention has the advantage of being shipped by air, whereas the pigment dispersions made with an alcohol solvent could not be so shipped. Also, the decreased weight of the dry coating mixture makes shipping it less expensive than shipping the pigment dispersion which contained an alcohol solvent.

We claim:

1. A dry powder edible film coating composition for use in pharmaceuticals, confectionery and food, comprising a dry mixture obtained by dry blending ingredients, including
    powerded particles of a film forming non-toxic edible polymer,
    Powered edible pigment particles,
    an edible polymer plasticizer, and
    a surfactant,
    said dry mixutre being capable of dispersion in a liquid without agglomeration to form a liquid coating dispersion.

2. A dry powder edible film coating composition for use in making a coating dispersion, including a solvent useful in pharmaceuticals, confectionery and food, comprising a dry mixture including
    powdered particles of a film forming non-toxic edible polymer,
    powdered edible pigment particles,
    an edible polymer plasticizer, and
    a surfactant for dispersing the plasticizer throughout said solvent of the coating dispersion,
    said dry mixture being solvent free,
    the polymer being methylcellulose, hydroxypropyl methylcellulose, hydroxypropyl cellulose, cellulose acetate phthalate, ethylcellulose, polyvinylpyrrolidone, sodium ethylcellulose sulphate, zein, or polyvinylacetatephthalate.

3. The dry edible film coating composition of claim 1, said pigment particles being FD&C and D&C lakes, titanium dioxide, magnesium carbonate, talc, pyrogenic silica, iron oxides, channel black, riboflavin, carmine 40, curcumin, annatto, or insoluble dyes.

4. The dry edible film coating composition of claim 1, said polymer placticizer being polyethylene glycol having a molecular weight in the range of 200 to 8000, glycerin, propyleneglycol, glycerinetriacetate, acetylated monoglyceride, triethylcitrate, tributylcitrate, acetyltriethylcitrate, acetyltributylcitrate, or diethyl phthalate.

5. The dry edible film coating composition of claim 1, said polymer plasticizer being polyethylene glycol 400.

6. The dry edible film coating composition of claim 1, the polymer plasticizer being a liquid plasticizer.

7. The dry edible film coating composition of claim 1, said surfactant being dioctyl sodium sufosuccinate, or polysorbate 80.

8. A dry powder edible film coating composition for use in making a coating dispersion, including a solvent useful in pharmaceuticals, confectionery and food, comprising a dry mixture including
    powdered particles of a film forming non-toxic edible polymer,
    powdered edible pigment particles,
    an edible polymer plasticizer, and
    a surfactant for dispersing the plasticizer throughout said solvent of the coating dispersion,
    said dry mixture being solvent free,
    the polymer being methylcellulose, hydroxypropyl methylcellulose, hydroxypropyl cellulose, cellulose acetate phthalate, ethylcellulose, polyvinylpyrrolidone, sodium ethylcellulose sulphate, zein, or polyvinylacetatephthalate,
    the pigment particles being FD&C and D&C lakes, titanium dioxide, magnexium carbonate, talc, pyrogenic silica, iron oxides, channel black, riboflavin, carmine 40, carcumin, annato, or insoluble dyes,
    said polymer plasticizer being polyethylene glycol having a molecular weight in the range of 200 to 8000, glycerin, propyleneglycol, glycerinetriacetate, acetylated monoglyceride, triethylcitrate, tributylcitrate, acetyltriethylcitrate, acetyltributylcitrate, or diethyl phthalate,
    said surfactant being dioctyl sodium sulfosuccinate, or polysorbate 80.

9. A method of making a dry powder edible film coating composition of powered pigment particles for use in pharmaceuticals, confectionary and food, comprising the steps of
    dry mixing a powder of a film forming polymer and powdered pigment particles in a blender,
    mixing a surfactant into a plasticizer,
    adding the surfactant-plasticizer mix to the blender containing the polymer-pigment mix and dry mixing until the combined mix is blended to form the dry edible film coating composition.

10. The method of making a dry powder edible film coating composition of claim 9,
    the polymer being methylcellulose, hydroxypropyl cellulose, hydroxypropyl methylcellulose, cellulose acetate phthalate, ethylcellulose, polyvinylpyrrollidone, sodium ethylcellulose sulphate, zein, or polyvinylacetatephthalate.

11. The method of making a dry edible film coating composition of claim 9,
    the pigment particles being FD&C and D&C lakes, titanium dioxide, magnesium carbonate, talc, pyrogenic silica, iron oxides, channel black, or insoluble dyes.

12. The method of making a dry edible film coating composition of claim 9,
    the polymer plasticizer being polyethylene glycol having a molecular weight in the range of 200 to 8000, glycerin, propyleneglycol, glycerintriacetate, acetylated monoglyceride, triethylcitrate, tributylcitrate, acetyltriethylcitrate, acetyltributylcitrate, or diethyl phthalate.

13. The method of making a dry edible film coating composition of claim 9,
the polymer plasticizer being polyethylene glycol 400.

14. The method of making a dry edible film coating composition of claim 9,
the polymer plasticizer being a liquid plasticizer.

15. The method of making a dry edible film coating composition of claim 9,
the surfactant being dioctyl sodium sulfosuccinate, or polysorbate 80.

16. The method of making a dry edible film coating in accordance with claim 9,
said polymer being methylcellulose, hydroxypropyl cellulose, hydroxyprophyl methylcellulose, cellulose acetate phthalate, ethylcellulose, polyvinypyrrollidone, sodium ethylcellulose sulphate, zein, or polyvinylacetatephthalate,
said pigment particles being FD&C and D&C lakes, titanium dioxide, magnesium carbonate, talc, pyrogenic silica, iron oxides, channel black, or insoluble dyes,
said polymer plasticizer being polyethylene glycol having a molecular weight in the range of 200 to 8000, glycerin, propyleneglycol, glycerintriacetate, acetylated monoglyceride, triethylcitrate, tributylcitrate, acetyltriethylcitrate, acetyltributylcitrate, or diethyl phthalate,
said surfactant being dioctyl sodium sulfosuccinate, or polysorbate 80.

17. A dry powder edible film coating composition for use in pharmaceuticals, confectionery and food, comprising a dry mixture including
Powdered particles of a film forming non-toxic edible polymer,
powdered edible pigment particles, and
An edible polymer plasticizer,
said dry mixture being solvent free.

18. The dry edible film coating composition of claim 17, the polymer being methylcellulose, hydroxpropyl methylcellulose, hydroxypropyl cellulose, cellulose acetate phthalate, ethylcellulose, polyvinylpyrrolidone, sodium ethylcellulose sulphate, zein, or polyvinylacetatephthalate.

19. The dry edible film coating composition of claim 17
said pigment particles being FD&C and D&C lakes, titanium dioxide, magnesium carbonate, talc, pyrogenic silica, iron oxides, channel black, riboflavin, carmine 40, curcumin, annatto, or insoluble dyes.

20. The dry edible film coating composition of claim 17,
said polymer plasticizer being polyethylene glycol having a molecular weight in the range of 200 to 8000, glycerin, propyleneglycol, glycerinetriacetate, acetylated monoglyceride, triethylcitrate, tributylcitrate, acetyltriethylcitrate, acetyltributylcitrate, or diethyl phthalate.

21. The dry edible film coating composition of claim 17,
said polymer plasticizer being polyethylene glycol 400.

22. The dry edible film coating composition of claim 17,
the polymer plasticizer being a liquid plasticizer.

23. The dry edible film coating composition of claim 17,
the polymer being methylcellulose, hydroxypropyl methylcellulose, hydroxypropyl cellulose, cellulose acetate phthalate, ethylcellulose, polyvinylpyrrolidone, sodium ethylcellulose sulphate, zein, polyvinylacetatephthalate,or methacrylic acid - methacrylic acid ester co-polymer,
the pigment particles being FD&C and D&C lakes, titanium dioxide, magnesium carbonate, talc, pyrogenic silica, iron oxides, channel black, riboflavin, carmine 40, curcumin, annatto, or insoluble dyes, and
said polymer plasticizer being polyethylene glycol having a molecular weight in the range of 200 to 8000, glycerin, propyleneglycol, glycerinetriacetate, acetylated monoglyceride, triethylcitrate, tributylcitrate, acetyltriethylcitrate, acetyltributylcitrate, diethyl phthalate, or mineral oil.

24. The dry edible film coating composition of claim 17,
the plasticizer being in the range of 1% to 30% by weight of the polymer,
the volume ratio of the polymer to pigment being about 4 to 1 to 10 to 1.

25. The dry edible film coating composition of claim 17,
the plasticizer being in the range of about 5% to 20% by weight of the polymer,
the volume ratio of the polymer to pigment being about 4 to 1 to 10 to 1.

26. The dry edible film coating composition of claim 17,
the plasticizer being about 10% by weight of the polymer,
the volume ratio of the polymer to pigment being about 6.5 to 1.

27. The dry edible film coating composition of claim 23,
the plasticizer being about 10% by weight of the polymer,
the volume ratio of the polymer to pigment being about 6.5 to 1.

28. A method of making a dry powder edible film coating composition of powdered pigment particles for use in pharmaceuticals, confectionery and food, comprising the steps of
dry mixing a powder of a film forming polymer and powdered pigment particles in a blender to form a polymer-pigment mix, and
adding a plasticizer to the blender containing the polymer-pigment mix and dry mixing until the combined mix is blended to form the dry edible film coating composition.

29. The method of making dry powder edible film coating composition of claim 28,
the polymer being methylcellulose, hydroxypropyl cellulose, hydroxypropyl, methylcellulose, cellulose acetate Phthalate, ethylcelluslose, polyvinylpyrrollidone, sodium ethylcellulose sulphate, zein, or polyvinylacetatephthalate.

30. The method of making a dry edible film coating composition of claim 28,
the pigment particles being FD&C and D&C lakes, titanium dioxide, magnesium carbonate, talc, pyrogenic silica, iron oxides, channel black, or insoluble dyes.

31. The method of making a dry edible film coating composition of claim 28,
the polymer plasticizer being polyethylene glycol having a molecular weight in the range of 200 to 8000, glycerin, propyleneglycol, glycerintriacetate, acetylated monoglyceride, triethylcitrate, tributylcitrate, acetyltriethylcitrate, acetyltributylcitrate, or diethyl phthalate.

32. The method of making a dry edible film coating composition of claim 28,
the polymer plasticizer being polyethylene glycol 400.

33. The method of making a dry edible film coating composition of claim 28,
the polymer plasticizer being a liquid plasticizer.

34. The method of making a dry edible film coating in accordance with claim 28,
said polymer being methycellulose, hydroxypropyl cellulose, hydroxypropyl methylcellulose, cellulose acetate phthalate, ethylcellulose, polyvinylpyrrollidone, sodium ethylcellulose sulphate, zein, or polyvinylacetatephthatlate,
said pigment particles being FD&C and D&C lakes, titanium dioxide magnesium carbonate, talc, pyrogenic silica, iron oxides, channel black, or insoluble dyes, and
said polymer plasticizer being polyethylene glycol having a molecular weight in the range of 200 to 8000, glycerin, propyleneglycol, glycerintriacetate, acetylated monoglyceride, triethylcitrate, tributylcitrate, acetyltriethylcitrate, acetyltributylcitrate, or diethyl phthalate.

35. The method of making a dry edible film coating composition of claim 28,
the plasticizer being in the range of 1% to 30% by weight of the polymer,
the volume ratio of the polymer to pigment being about 4 to 1 to 10 to 1.

36. The method of claim 28,
the plasticizer being in the range of about 5% to 20% by weight of the polymer,
the volume ratio of the polymer to pigment being about 4 to 1 to 10 to 1.

37. The method of claim 28,
the plasticizer being about 10% by weight of the polymer,
the volume ratio of the polymer to pigment being about 6.5 to 1.

38. The method of claim 34,
the plasticizer being about 10% by weight of the polymer,
the volume ratio of the polymer to pigment being about 6.5 to 1.

39. A dry powder edible film coating composition for use in pharmaceuticals, confectionery and food, comprising a dry mixture including
500 grams of powdered hydroxypropyl methylcellulose,
750 grams of powdered titanium dioxide, and
150 grams of polyethylene glycol 400,
said polyethylene glycol 400 being thoroughly mixed with the hydroxypropyl methylcellulose and the titanium dioxide to form a coating mixture.

40. A dry powder edible film coating composition for use in pharmaceuticals, confectionery and food, comprising a dry mixture including
1500 grams of powdered hydroxypropyl methylcellulose,
250 grams of titanium dioxide,
150 grams of FD&C Yellow No. 6 aluminum lake,
50 grams of FD&C Red No. 3 aluminum lake,
50 grams of FD&C Blue No. 2 aluminum lake, and
150 grams of polyethylene glycol 400,
said polyethylene glycol 400 being thoroughly mixed with the other ingredients to form a coating mixture.

41. A method of making a coating dispersion for use in pharmaceuticals, confectionery and food, comprising the steps of
dry mixing 1500 grams of powdered hydroxypropyl methylcellulose and 750 grams of powdered titanium dioxide in a blender to form a polymer-pigment mix,
adding 150 grams of polyethylene glycol 400 to the blender containing the polymer-pigment mix, and
dry mixing until the combined mix is blended to form a dry edible film coating composition.

42. A method of making a coating dispersion for use in pharmaceuticals, confectionery and food, comprising the steps of
dry mixing 1500 grams of hydroxypropyl cellulose in a blender with 250 grams of titanium dioxide, 150 grams of FD&C Yellow No. 6 aluminum lake, 50 grams of FD&C Red No. 3 aluminum lake, and 50 grams of FD&C Blue No. 2 aluminum lake, to form a polymer-pigment mix,
adding 150 grams of polyethylene glycol 400 to the blender containing the polymer-pigment mix,
adding 10 grams of fumed silica to the mix, and
dry mixing until the combined mix is blended to form a dry edible film coating composition.

43. A dry powder edible film coating composition produced by the method of claim 9.

44. A dry powder edible film coating composition produced by the method of claim 10.

45. A dry powder edible film coating composition produced by the method of claim 11.

46. A dry powder esdible film coating composition produced by the method of claim 12.

47. A dry powder edible film coating composition produced by the method of claim 13.

48. A dry powder edible film coating composition produced by the method of claim 14.

49. A dry powder edible film coating composition produced by the method of claim 15.

50. A dry powder edible film coating composition produced by the method of claim 16.

51. A dry powder edible film coating composition produced by the method of claim 28.

52. A dry powder edible film coating composition produced by the method of claim 29.

53. A dry powder edible film coating composition produced by the method of claim 30.

54. A dry powder edible film coating composition produced by the method of claim 31.

55. A dry powder edible film coating composition produced by the method of claim 32.

56. A dry powder edible film coating composition produced by the method of claim 33.

57. A dry powder edible film coating composition produced by the method of claim 34.

58. A dry powder edible film coating composition produced by the method of claim 35.

59. A dry powder edible film coating composition Produced by the method of claim 36.

60. A dry powder edible film coating composition produced by the method of claim 37.

61. A dry powder edible film coating composition produced by the method of claim 38.

62. A dry powder edible film coating composition produced by the method of claim 41.

63. A dry powder edible film coating composition produced by the method of claim 42.

* * * * *